US006838414B2

(12) United States Patent
Gesing et al.

(10) Patent No.: US 6,838,414 B2
(45) Date of Patent: Jan. 4, 2005

(54) SUBSTITUTED ARYL SULPHONYL(THIO) UREAS USED AS HERBICIDES

(75) Inventors: Ernst Rudolf F. Gesing, Erkrath (DE); Rolf Kirsten, Monheim (DE); Joachim Kluth, Langenfeld (DE); Klaus-Helmut Müller, Düsseldorf (DE); Mark Wilhelm Drewes, Langenfeld (DE); Johannes Rudolf Jansen, Monheim (DE); Ulrich Philipp, Köln (DE); Hans-Jochem Riebel, Wuppertal (DE); Otto Schallner, Monheim (DE); Markus Dollinger, Overland Park, KS (US); Hans-Joachim Santel, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/195,979

(22) Filed: Jul. 16, 2002

(65) Prior Publication Data

US 2003/0153463 A1 Aug. 14, 2003

Related U.S. Application Data

(62) Division of application No. 09/125,997, filed as application No. PCT/EP97/00798 on Feb. 20, 1997, now Pat. No. 6,451,737.

(30) Foreign Application Priority Data

Mar. 5, 1996 (DE) .......................... 196 08 445

(51) Int. Cl.⁷ ...................... A01N 43/54; C07D 239/697
(52) U.S. Cl. ...................... 504/214; 504/215; 504/243; 544/331; 544/332; 544/323; 544/324; 544/320; 544/321
(58) Field of Search .................. 504/214, 215, 504/243; 544/331, 323, 324, 320, 321, 332

(56) References Cited

U.S. PATENT DOCUMENTS

| 4,120,691 A | 10/1978 | Levitt | 71/93 |
|---|---|---|---|
| 4,169,719 A | 10/1979 | Levitt | 71/92 |
| 4,425,153 A | 1/1984 | Adams, Jr. | 71/92 |
| 4,452,628 A | 6/1984 | Adams, Jr. | 71/93 |
| 4,786,311 A | 11/1988 | Levitt | 544/212 |
| 5,723,409 A | * 3/1998 | Schnabel et al. | 544/321 |

FOREIGN PATENT DOCUMENTS

| EP | 0 023 422 | 2/1981 |
|---|---|---|
| EP | 0 044 212 A1 | 1/1982 |
| EP | 0 044 807 | 1/1982 |
| EP | 0 044 808 A2 | 1/1982 |
| EP | 0 070 802 A2 | 1/1983 |
| EP | 0 084 020 A2 | 7/1983 |
| EP | 0 094 790 A2 | 11/1983 |
| EP | 0 096 002 | 12/1983 |
| WO | WO 92/09608 | 6/1992 |
| WO | WO 92/14715 | 9/1992 |
| WO | WO 93/16998 | 9/1993 |
| WO | WO 93/17001 | 9/1993 |
| WO | WO 94/11358 | 5/1994 |

OTHER PUBLICATIONS

Chemical Abstracts, vol. 124, No. 15, Apr. 9, 1996, abstract No. 196428, Sung, Nack–Do et al., "Herbicidal activity and persistency in aqueous solution of ortho– disubstituted benzenesulfonylurea derivatives".

* cited by examiner

Primary Examiner—Richard L. Raymond
(74) Attorney, Agent, or Firm—Norris McLaughlin & Marcus PA

(57) ABSTRACT

The invention relates to novel substituted arylsulphonyl (thio)ureas (I)

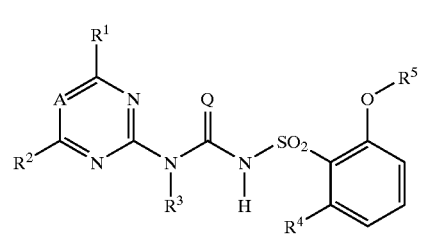

in which

A represents nitrogen or a CH grouping,

Q represents oxygen or sulphur, $R^1$ represents hydrogen, halogen or respectively optionally substituted alkyl, alkoxy, alkylthio, alkylamino, dialkylamino, cycloalkyl, cycloalkyloxy or heterocyclyloxy, $R^2$ represents hydrogen, halogen or respectively optionally substituted alkyl, alkoxy, alkylthio, alkylamino, dialkylamino, cycloalkyl, cycloalkyloxy or heterocyclyloxy, $R^3$ represents hydrogen or optionally substituted alkyl, $R^4$ represents respectively optionally substituted alkyl, alkoxy, alkenyl, alkinyl, alkenyloxy, alkinyloxy, cycloalkyl, cycloalkyloxy or cycloalkylalkyl, and $R^5$ represents hydrogen, formyl or respectively optionally substituted alkyl, alkylcarbonyl, alkoxycarbonyl, alkylsulphonyl, alkenyl, alkinyl, cycloalkyl, cycloalkylcarbonyl, cycloalkylsulphonyl or heterocyclyl, and to salts of compounds of the formula (I), except for the compound N-(4,6-dimethyl-pyrimidin-2-yl)-N'-[2-(1,1,2,2-tetrafluoro-ethoxy)-6-methyl-phenylsulphonyl]-urea, to processes for preparing the novel compounds and to their use as herbicides.

9 Claims, No Drawings

SUBSTITUTED ARYL SULPHONYL(THIO) UREAS USED AS HERBICIDES

This application is a divisional of application Ser. No. 09/125,997, filed on Aug. 28, 1998, now U.S. Pat. No. 6,451,737, which is a 371 application of PCT/EP97/00798, filed on Feb. 20, 1997.

The present invention relates to novel substituted arylsulphonyl(thio)ureas, to processes for their preparation and to their use as herbicides.

It is already known that certain substituted sulphonylureas have herbicidal properties (cf. DE 2715786, EP 1514, EP 23422). However, the herbicidal activity and the crop plant safety of these compounds is not satisfactory in all aspects.

This invention, accordingly, provides the novel substituted arylsulphonyl(thio)ureas of the general formula (I)

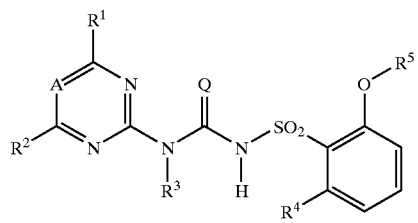

(I)

in which

A represents nitrogen or a CH grouping,

Q represents oxygen or sulphur, $R^1$ represents hydrogen, halogen or respectively optionally substituted alkyl, alkoxy, alkylthio, alkylamino, dialkylamino, cycloalkyl, cycloalkyloxy or heterocyclyloxy, $R^2$ represents hydrogen, halogen or respectively optionally substituted alkyl, alkoxy, alkylthio, alkylamino, dialkylamino, cycloalkyl, cycloalkyloxy or heterocyclyloxy, $R^3$ represents hydrogen or optionally substituted alkyl, $R^4$ represents respectively optionally substituted alkyl, alkoxy, alkenyl, alkinyl, alkenyloxy, alkinyloxy, cycloalkyl, cycloalkyloxy or cycloalkylalkyl, and $R^5$ represents hydrogen, formyl or respectively optionally substituted alkyl, alkylcarbonyl, alkoxycarbonyl, alkylsulphonyl, alkenyl, alkinyl, cycloalkyl, cycloalkylcarbonyl, cycloalkylsulphonyl or heterocyclyl, and salts of compounds of the formula (I), except for the prior-art compound N-(4,6-dimethyl-pyrimidin-2-yl)-N'-[2-(1,1,2,2-tetra-fluoro-ethoxy)-6-methyl-phenylsulphonyl]-urea (cf. EP 23422) which is excluded by disclaimer.

The novel substituted arylsulphonyl(thio)ureas of the general formula (I) are obtained when (a) aminoazines of the general formula (II)

(II)

in which

A, $R^1$ and $R^2$ are each as defined above, are reacted with arylsulphonyl iso(thio)cyanates of the general formula (III)

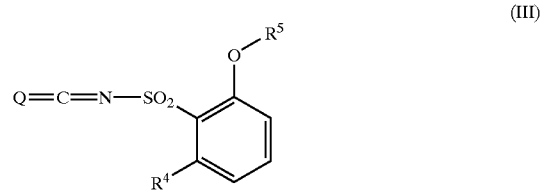

(III)

in which

Q, $R^4$ and $R^5$ are each as defined above, if appropriate in the presence of a reaction auxiliary and if appropriate in the presence of a diluent, or (b) substituted aminoazines of the general formula (IV)

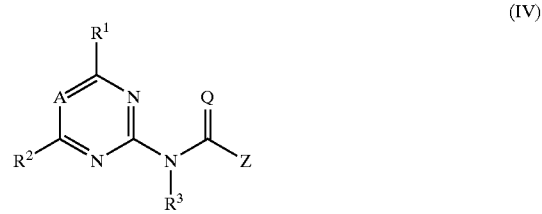

(IV)

in which

A, Q, $R^1$ and $R^2$ are each as defined above,

Z represents halogen, alkoxy or aryloxy and $R^3$ is as defined above or represents the grouping —C(Q)—Z are reacted with arenesulphonamides of the general formula (V)

(V)

in which $R^4$ and $R^5$ are each as defined above, if appropriate in the presence of a reaction auxiliary and if appropriate in the presence of a diluent, or (c) aminoazines of the general formula (II)

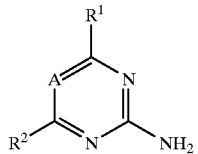

(II)

in which

A, $R^1$ and $R^2$ are each as defined above, are reacted with substituted arenesulphonamides of the general formula (VI)

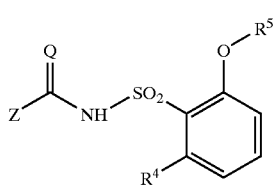

(VI)

in which

Q, $R^4$ and $R^5$ are each as defined above and

Z represents halogen, alkoxy or aryloxy, if appropriate in the presence of a reaction auxiliary and if appropriate in the presence of a diluent, and the compounds of the formula (I) obtained by processes (a), (b) and (c) are, if appropriate, converted into salts by customary methods.

The novel substituted arylsulphonyl(thio)ureas of the general formula (I) have strong herbicidal activity.

The invention preferably provides compounds of the formula (I) in which

A represents nitrogen or a CH grouping,

Q represents oxygen or sulphur, $R^1$ represents hydrogen, halogen, represents respectively optionally cyano-, halogen- or $C_1$–$C_4$-alkoxy-substituted alkyl, alkoxy, alkylthio, alkylamino or di-alkylamino having in each case 1 to 4 carbon atoms in the alkyl groups, represents respectively optionally cyano-, halogen-, $C_1$–$C_4$-alkyl- or $C_1$–$C_4$-alkoxy-substituted cycloalkyl or cycloalkyloxy having in each case 3 to 6 carbon atoms, or represents respectively optionally cyano-, halogen-, $C_1$–$C_4$-alkyl- or $C_1$–$C_4$-alkoxy-substituted oxetanyloxy, furyloxy or tetrahydrofuryloxy.

$R^2$ represents hydrogen or halogen, represents respectively optionally cyano-, halogen- or $C_1$–$C_4$-alkoxy-substituted alkyl, alkoxy, alkylthio, alkylamino or di-alkylamino having in each case 1 to 4 carbon atoms in the alkyl groups, represents respectively optionally cyano-, halogen-, $C_1$–$C_4$-alkyl- or $C_1$–$C_4$-alkoxy-substituted cycloalkyl or cycloalkyloxy having in each case 3 to 6 carbon atoms, or represents respectively optionally cyano-, halogen-, $C_1$–$C_4$-alkyl- or $C_1$–$C_4$-alkoxy-substituted oxetanyloxy, furyloxy or tetrahydrofuryloxy, $R^3$ represents hydrogen or optionally $C_1$–$C_4$-alkoxy, $C_1$–$C_4$-alkyl-carbonyl- or $C_1$–$C_4$-alkoxy-carbonyl-substituted alkyl having 1 to 4 carbon atoms, $R^4$ represents respectively optionally cyano-, halogen- or $C_1$–$C_4$-alkoxy-substituted alkyl or alkoxy having in each case 1 to 6 carbon atoms in the alkyl groups, represents respectively optionally halogen-substituted alkenyl, alkinyl, alkenyloxy or alkinyloxy having in each case 2 to 6 carbon atoms in the alkenyl or alkinyl groups, or represents respectively optionally cyano-, halogen- or $C_1$–$C_4$-alkyl-substituted cycloalkyl, cycloalkyloxy or cycloalkylalkyl having in each case 3 to 6 carbon atoms in the cycloalkyl groups and optionally 1 to 4 carbon atoms in the alkyl moiety, $R^5$ represents hydrogen, formyl, represents respectively optionally cyano-, halogen- or $C_1$–$C_4$-alkoxy-substituted alkyl, alkylcarbonyl, alkoxycarbonyl or alkylsulphonyl having in each case 1 to 6 carbon atoms in the alkyl groups, represents respectively optionally halogen-substituted alkenyl or alkinyl having in each case 2 to 6 carbon atoms, represents respectively optionally cyano-, halogen- or $C_1$–$C_4$-alkyl-substituted cycloalkyl, cycloalkylcarbonyl or cycloalkylsulphonyl having in each case 3 to 6 carbon atoms in the cycloalkyl groups, or represents respectively optionally cyano-, halogen-, $C_1$–$C_4$-alkyl- or $C_1$–$C_4$-alkoxy-substituted oxetanyl, furyl or tetrahydrofuryl, except for the prior-art compound N-(4,6-dimethyl-pyrimidin-2-yl)-N'-[2-(1,1,2,2-tetrafluoro-ethoxy)-6-methyl-phenylsulphonyl]-urea (cf. EP 23422) which is excluded by disclaimer.

The invention furthermore preferably provides sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salts of compounds of the formula (I) in which A, Q, $R^1$, $R^2$, $R^3$, $R^4$ and $R^5$ are each preferably as defined above.

The invention provides in particular compounds of the formula (I) in which

A represents nitrogen or a CH grouping,

Q represents oxygen or sulphur, $R^1$ represents hydrogen, fluorine, chlorine, bromine or respectively optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylamino, ethylamino, n- or i-propylamino, dimethylamino or diethylamino, $R^2$ represents fluorine, chlorine, bromine or respectively optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylamino, ethylamino, n- or i-propylamino, dimethylamino or diethylamino, $R^3$ represents hydrogen or optionally methoxy-, ethoxy-, n- or i-propoxy-, acetyl-, propionyl-, n- or i-butyroyl-, methoxycarbonyl-, ethoxycarbonyl-, n- or i-propoxycarbonyl-substituted methyl or ethyl, $R^4$ represents respectively optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, represents respectively optionally fluorine-, chlorine- or bromine-substituted propenyl, butenyl, propinyl, butinyl, propenyloxy, butenyloxy, propinyloxy or butinyloxy, or represents respectively optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl or cyclohexylmethyl, $R^5$ represents hydrogen, formyl, represents respectively optionally cyano-, fluorine-, chlorine-, methoxy-, ethoxy-, n- or i-propoxy-substituted methyl, ethyl, n- or i-propyl, n-, i-, s- or t-butyl, acetyl, propionyl, n- or i-butyroyl, methoxycarbonyl ethoxycarbonyl, n- or i-propoxycarbonyl, methylsulphonyl, ethylsulphonyl, n- or i-propylsulphonyl, represents respectively optionally fluorine-, chlorine- or bromine-substituted propenyl, butenyl, propinyl or butinyl, or represents respectively optionally cyano-, fluorine-, chlorine-, bromine-, methyl-, ethyl-, n- or i-propyl-substituted cyclopropyl, cyclobutyl, cyclopentyl, cyclohexyl, cyclopropylcarbonyl, cyclobutylcarbonyl, cyclopentylcarbonyl, cyclohexylcarbonyl, cyclopropylsulphonyl, cyclobutylsulphonyl, cyclopentylsulphonyl or cyclohexylsulphonyl, except for the prior-art compound N-(4,6-dimethyl-pyrimidin-2-yl)-N'-[2-(1,1,2,2-tetrafluoro-ethoxy)-6-methyl-phenylsulphonyl]-urea (cf. EP 23422) which is excluded by disclaimer.

The abovementioned general or preferred radical definitions apply both to the end products of the formula (I) and, correspondingly, to the starting materials or intermediates required in each case for the preparation. These radical definitions can be combined with one another as desired, that is to say combinations between the ranges of preferred compounds indicated are also possible.

Examples of the compounds of the formula (I) according to the invention are listed in the groups below.

Group 1

(Ia-1)

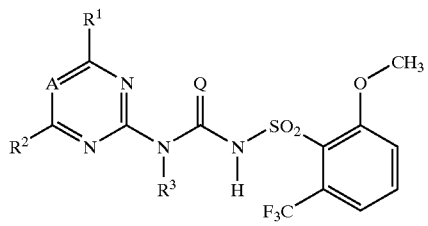

A, Q, $R^1$, $R^2$ and $R^3$ have, for example, the meaning listed below:

| A | Q | $R^1$ | $R^2$ | $R^3$ |
|---|---|---|---|---|
| CH | O | OCH$_3$ | OCH$_3$ | H |
| CH | O | CH$_3$ | OCH$_3$ | H |
| CH | O | CH$_3$ | CH$_3$ | H |
| CH | O | Cl | OCH$_3$ | H |
| CH | O | H | CH$_3$ | H |
| N | O | CH$_3$ | OCH$_3$ | CH$_3$ |
| N | O | OCH$_3$ | OCH$_3$ | CH$_3$ |
| N | O | CH$_3$ | OCH$_3$ | H |
| N | O | OCH$_3$ | OCH$_3$ | H |
| N | O | CH$_3$ | CH$_3$ | H |
| N | O | OCHF$_2$ | N(CH$_3$)$_2$ | H |
| N | O | CH$_3$ | SCH$_3$ | H |
| N | O | C$_2$H$_5$ | OCH$_3$ | H |
| N | O | CH$_3$ | OC$_2$H$_5$ | H |
| N | O | H | OCH$_3$ | H |
| N | O | OCH$_3$ |  | H |

-continued (Ia-1)

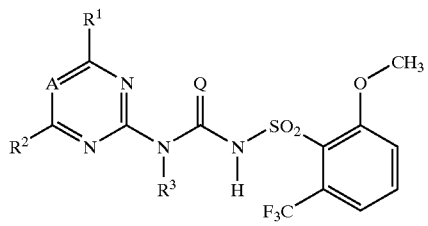

A, Q, $R^1$, $R^2$ and $R^3$ have, for example, the meaning listed below:

| A | Q | $R^1$ | $R^2$ | $R^3$ |
|---|---|---|---|---|
| N | O | CH$_3$ | N(CH$_3$)$_2$ | H |
| CH | O | OCH$_3$ | ![oxetane] | H |
| CH | O | ![oxetane] | ![oxetane] | H |
| CH | O | CH$_3$ | ![oxetane] | H |
| CH | O | Cl | ![oxetane] | H |
| N | O | ![oxetane] | ![oxetane] | H |
| N | O | CH$_3$ | ![oxetane] | H |
| N | O | H | ![oxetane] | H |
| N | S | CH$_3$ | OCH$_3$ | H |

Group 2

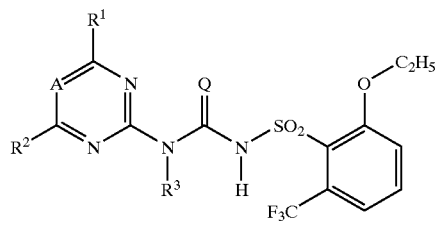
(IA-2)

A, Q, R¹, R² and R³ have, for example, the meaning given above in group 1.

Group 3

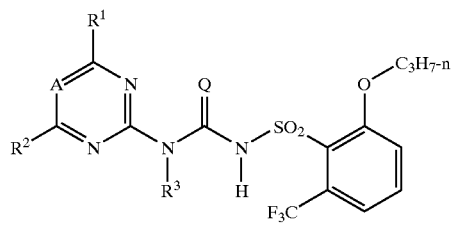
(IA-3)

A, Q, R¹, R² and R³ have, for example, the meaning given above in group 1.

Group 4

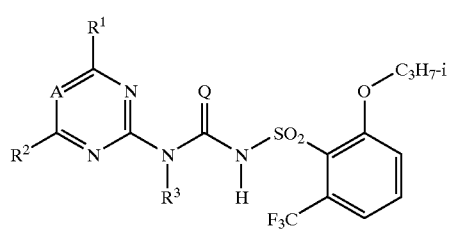
(IA-4)

A, Q, R¹, R² and R³ have, for example, the meaning given above in group 1.

Group 5

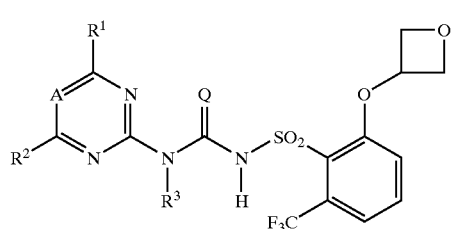
(IA-5)

A, Q, R¹, R² and R³ have, for example, the meaning given above in group 1.

Group 6

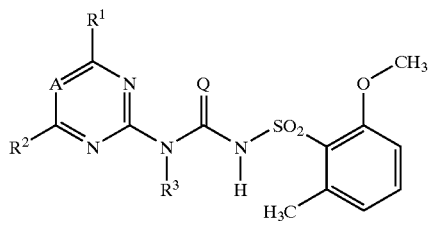
(IA-6)

A, Q, R¹, R² and R³ have, for example, the meaning given above in group 1.

Group 7

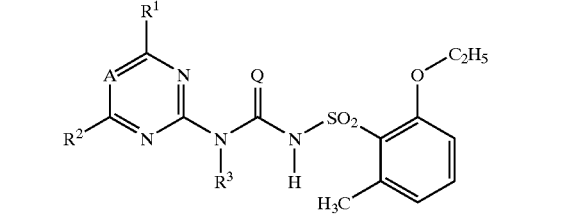
(IA-7)

A, Q, R¹, R² and R³ have, for example, the meaning given above in group 1.

Group 8

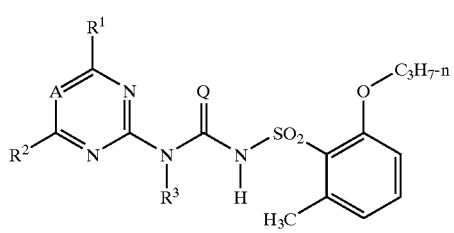
(IA-8)

A, Q, R¹, R² and R³ have for example, the meaning given above in group 1.

Group 9

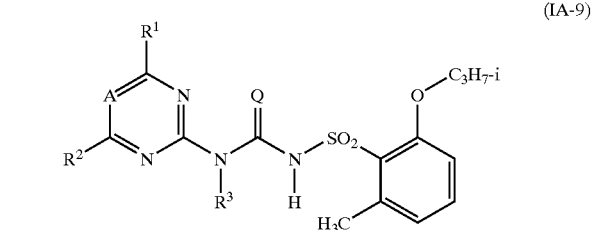
(IA-9)

A, Q, R¹, R² and R³ have for example, the meaning given above in group 1.

Group 10

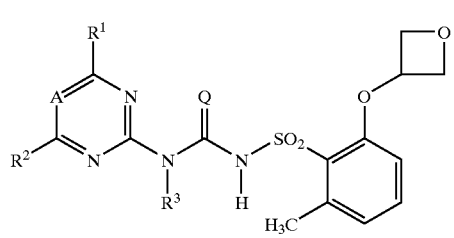
(IA-10)

A, Q, R¹, R² and R³ have for example, the meaning given above in group 1.

Group 11

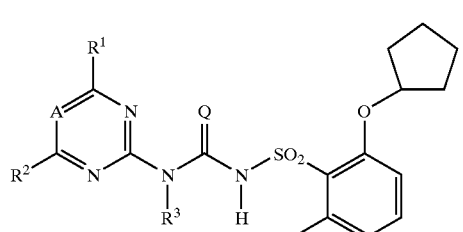
(IA-11)

A, Q, R¹, R² and R³ have, for example, the meaning given above in group 1.

Group 12

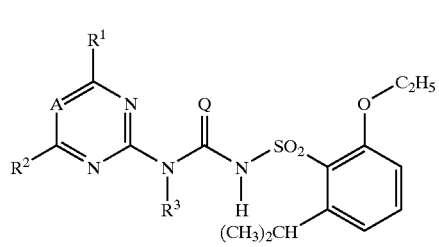
(IA-12)

A, Q, R¹, R² and R³ have, for example, the meaning given above in group 1.

Group 13

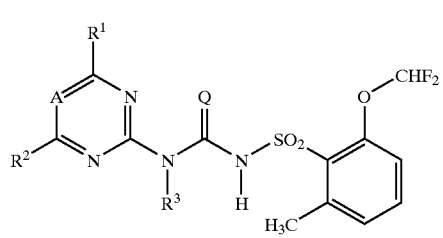
(IA-13)

A, Q, R¹, R² and R³ have, for example, the meaning given above in group 1.

Group 14

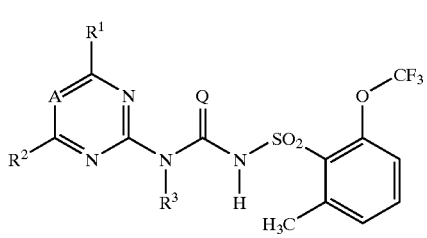
(IA-14)

A, Q, R¹, R² and R³ have, for example, the meaning given above in group 1.

Using, for example, 2-amino-4-methoxy-6-methyl-pyrimidine and 2-ethoxy-6-trifluoromethyl-phenylsulphonyl isocyanate as starting materials, the course of the reaction in the process (a) according to the invention can be illustrated by the following equation:

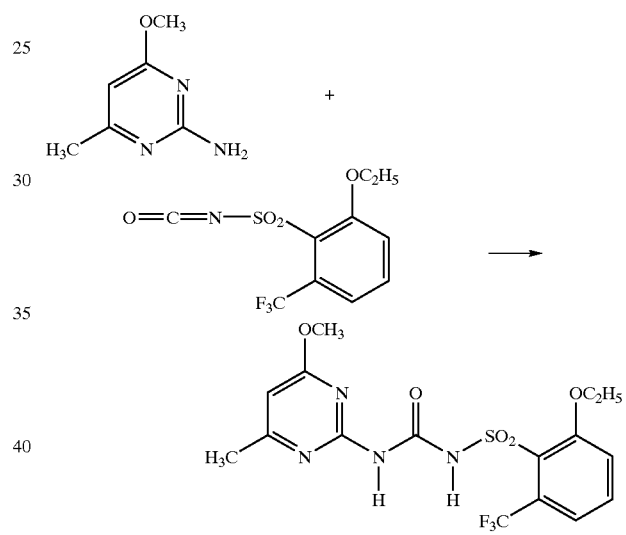

Using, for example, 2-methoxycarbonylamino-4-methoxy-6-trifluoromethyl-1,3,5-triazine and 2-methyl-6-trifluoromethoxy-benzenesulphonamide as starting materials, the course of the reaction in the process (b) according to the invention can be illustrated by the following equation:

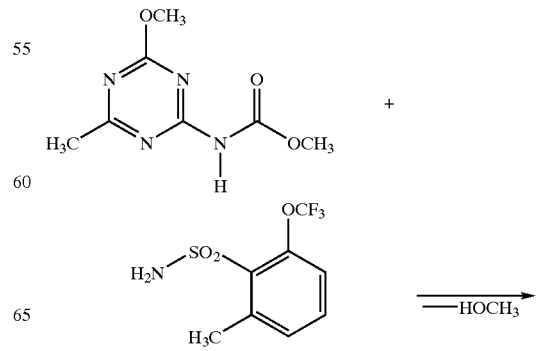

-continued

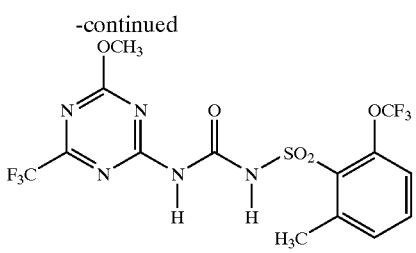

Using, for example, 2-amino-4-chloro-6-methoxy-pyrimidine and N-(2,6-dimethoxy-phenylsulphonyl)-O-phenyl-urethane as starting materials, the course of the reaction in the process (c) according to the invention can be illustrated by the following equation:

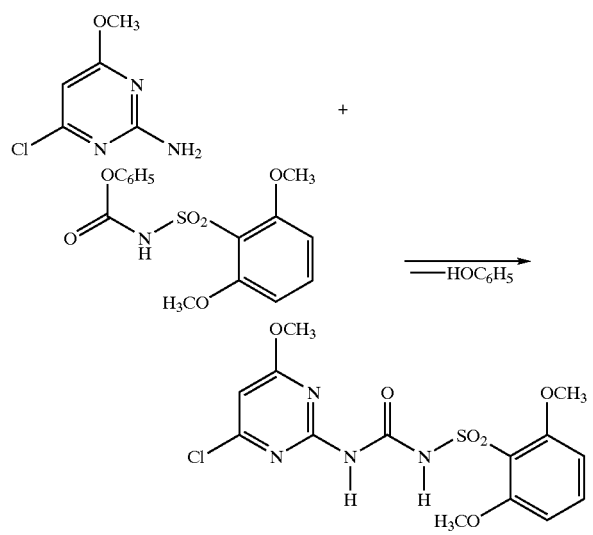

The formula (II) provides a general definition of the aminoazines to be used as starting materials in the processes (a) and (c) for preparing compounds of the general formula (I). In the formula (II), A, $R^1$ and $R^2$ each preferably or in particular have those meanings which have already been indicated above, in connection with the description of the compounds of the formula (I), as being preferred or particularly preferred for A, $R^1$ and $R^2$.

The aminoazines of the formula (II) are known chemicals for synthesis, some of which are commercially available.

The formula (III) provides a general definition of the arylsulphonyl iso(thio)cyanates further to be used as starting materials in the process (a) according to the invention. In the formula (III), Q, $R^4$ and $R^5$ each preferably or in particular have those meanings which have already been indicated above, in connection with the description of the compounds of the formula (I), as being preferred or particularly preferred for Q, $R^4$ and $R^5$.

The starting materials of the formula (III) are known and/or can be prepared by processes known per se (cf. DE 3208189, EP 23422, EP 64322, EP 44807, EP 216504, Preparation Examples).

The arylsulphonyl iso(thio)cyanates of the formula (III) are obtained when arenesulphonamides of the general formula (V)—above—are reacted with phosgene or thiophosgene, if appropriate in the presence of an alkyl isocyanate, such as, for example, butyl isocyanate, if appropriate in the presence of a reaction auxiliary, such as, for example, diazabicyclo[2.2.2]-octane, and in the presence of a diluent, such as, for example, toluene, xylene or chlorobenzene, at temperatures between 80° C. and 150° C., and the volatile components are distilled off under reduced pressure after the reaction has ended.

The formula (IV) provides a general definition of the substituted aminoazines to be used as starting materials in the process (b) according to the invention for preparing compounds of the formula (I). In the formula (IV), A, Q, $R^1$ and $R^2$ each preferably or in particular have those meanings which have already been indicated above, in connection with the description of the compounds of the formula (I), as being preferred or particularly preferred for A, Q, $R^1$ and $R^2$; Z preferably represents fluorine, chlorine, bromine, $C_1$–$C_4$-alkoxy or phenoxy, in particular chlorine, methoxy, ethoxy or phenoxy.

The starting materials of the formula (IV) are known and/or can be prepared by processes known per se (cf. U.S. Pat. No. 4,690,707, DE 19501174, Preparation Examples).

The formula (V) provides a general definition of the arenesulphonamides further to be used as starting materials in the process (b) according to the invention. In the formula (V), $R^4$ and $R^5$ each preferably or in particular have those meanings which have already been indicated above, in connection with the description of the compounds of the formula (I), as being preferred or particularly preferred for $R^4$, and $R^5$.

The starting materials of the formula (V) are known and/or can be prepared by a process known per se (cf. DE 3208189, EP 23422, EP 64322, EP 44807, EP 216504, DE 19525162, Preparation Examples).

The formula (VI) provides a general definition of the substituted arenesulphonamides to be used as starting materials in the process (c) according to the invention for preparing the compounds of the formula (I). In the formula (VI), Q, $R^4$ and $R^5$ each preferably or in particular have those meanings which have already been indicated above, in connection with the description of the compounds of the formula (I), as being preferred or particularly preferred for Q, $R^4$ and $R^5$; Z preferably represents fluorine, chlorine, bromine, $C_1$–$C_4$-alkoxy or phenoxy, in particular chlorine, methoxy, ethoxy or phenoxy.

The starting materials of the formula (VI) are known and/or can be prepared by processes known per se (cf. the Preparation Examples).

Suitable diluents for carrying out the processes (a), (b) and (c) according to the invention are inert organic solvents. These include in particular aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl or diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate; sulphoxides, such as dimethyl sulphoxide; alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

The processes (a), (b) and (c) according to the invention are preferably carried out in the presence of a suitable reaction auxiliary. Suitable reaction auxiliaries are all customary inorganic or organic bases. These include, for example, alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

When carrying out the processes (a), (b) and (c) according to the invention, the reaction temperatures can be varied within a relatively wide range. In general, the reaction is carried out at temperatures between −20° C. and +150° C., preferably between 0° C. and +120° C.

The processes (a), (b) and (c) according to the invention are generally carried out under atmospheric pressure. However, it is also possible to carry out the process according to the invention under elevated or reduced pressure—generally between 0.1 bar and 10 bar.

In the practice of the processes (a), (b) and (c) according to the invention, the starting materials are generally employed in approximately equimolar amounts. However, it is also possible to employ one of the components in a relatively large excess. The reaction is generally carried out in a suitable diluent in the presence of a reaction auxiliary, and the reaction mixture is generally stirred for a number of hours at the temperature required. Work-up is carried out by customary methods (cf. the Preparation Examples).

If required, salts can be prepared from the compounds of the general formula (I) according to the invention. Such salts are obtained in a simple manner by customary methods of forming salts, for example by dissolving or dispersing a compound of the formula (I) in a suitable solvent, such as, for example, methylene chloride, acetone, tert-butyl methyl ether or toluene, and addition of a suitable base. The salts can then be isolated—if required after prolonged stirring—by concentration or filtration with suction.

The active compounds according to the invention can be used as defoliants, desiccants, haulm killers and, especially, as weed killers. By weeds in the broadest sense, there are to be understood all plants which grow in locations where they are undesirable. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crop plants of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crop plants of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and railway tracks, and on paths and squares with or without tree plantings. Likewise, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, sports fields and pastureland, and for the selective control of weeds in annual cultures.

The compounds of the formula (I) according to the invention are suitable in particular for controlling monocotyledonous and dicotyledenous weeds, both pre-emergence and post-emergence. They have strong herbicidal activity and a broad spectrum of activity when applied to the soil and to the above-ground parts of plants.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersing agents and/or foam-forming agents.

If the extender used is water, it is also possible to employ for example organic solvents as auxiliary solvents. Essentially, suitable liquid solvents are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are:
for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifiers and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 percent by weight of active compound, preferably between 0.5 and 90%.

For controlling weeds, the active compounds according to the invention, such as or in the form of their formulations, can also be used as mixtures with known herbicides, finished formulations or tank mixes being possible.

Possible components for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxyphenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the examples below.

PREPARATION EXAMPLES

Example 1

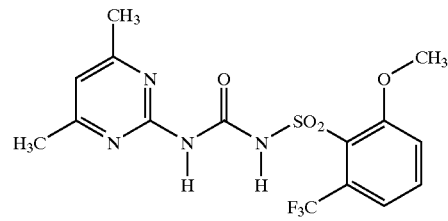

(Process (b))

At about 20° C., a mixture of 1.43 g (5.6 mmol) of 2-methoxy-6-trifluoromethyl-benzenesulphonamide, 1.24 g (5.1 mmol) of 2-phenoxycarbonylamino-4,6-dimethyl-pyrimidine, 0.85 g (5.6 mmol) of diazabicycloundecene (DBU) and 50 ml of acetonitrile is stirred for 15 hours. The mixture is then concentrated using water pump vacuum and the residue is stirred with 50 ml of 1N hydrochloric acid and 50 ml of methylene chloride. The organic phase is separated off, washed with water, dried with sodium sulphate and filtered. The filtrate is concentrated using water pump vacuum, the residue is digested with i-propanol and the crystalline product is isolated by filtration with suction.

This gives 1.6 g (62% of theory) of N-(4,6-dimethyl-pyrimidin-2-yl)-N'-(2-methoxy-6-trifluoromethyl-phenylsulphonyl)-urea of melting point 190° C.

Example 2

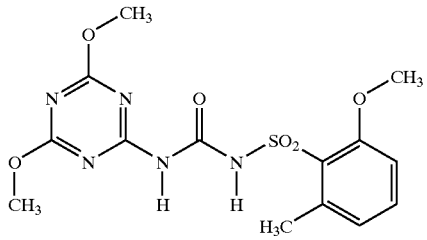

(Process (b))

At about 20° C., a mixture of 2.0 g (10 mmol) of 2-methoxy-6-methyl-benzenesulphonamide, 4.0 g (10 mmol) of N,N-bis-phenoxycarbonyl-2-amino-4,6-dimethoxy-1,3,5-triazine, 1.1 g (10 mmol) of potassium t-butoxide and 50 ml of acetonitrile is stirred for 15 hours. The mixture is then concentrated using water pump vacuum and the residue is stirred with 50 ml of 1N hydrochloric acid and 50 ml of methylene chloride. The organic phase is separated off, washed with water, dried with sodium sulphate and filtered. The filtrate is concentrated using water pump vacuum, the residue is digested with i-propanol and the resulting crystalline product is isolated by filtration with suction.

This gives 2.1 g (55% of theory) of N-(4,6-dimethoxy-1,3,5-triazin-2-yl)-N'-(2-methoxy-6-methyl-phenylsulphonyl)-urea of melting point 163° C.

Example 3

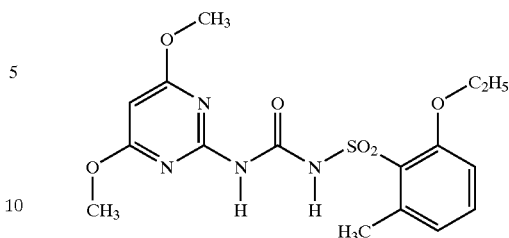

(Process (c) with precursor)

At about 20° C., 1.6 g (10 mmol) of phenyl chloroformate are added dropwise to a mixture of 2.2 g (10 mmol) of 2-ethoxy-6-methyl-benzenesulphonamide, 2.0 g (20 mmol) of triethylamine and 30 ml of acetonitrile, and the mixture is stirred at the temperature stated for about 30 minutes. 1.0 g (10 mmol) of methanesulphonic acid and 1.6 g (10 mmol) of 2-amino-4,6-dimethoxy-pyrimidine are then added, and the reaction mixture is stirred at about 60° C. for about 15 minutes. The mixture is cooled to about 20° C. and filtered with suction, the filtrate is concentrated using water pump vacuum and the residue is stirred with 30 ml of 1N hydrochloric acid. Filtration with suction and drying gives a crude product which is purified by rinsing with diethyl ether.

Yield: 2.2 g (55%) of theory) of N-(4,6-dimethoxy-pyrimidin-2-yl)-N'-(2-ethoxy-6-methyl-phenylsulphonyl)-urea of melting point 184° C.

Similar to Preparation Examples 1 to 3, and in accordance with the general description of the preparation processes according to the invention, it is also possible to prepare, for example, the compounds of the formula (I) listed in Table 1 below.,

TABLE 1

Examples of compounds of the formula (I)

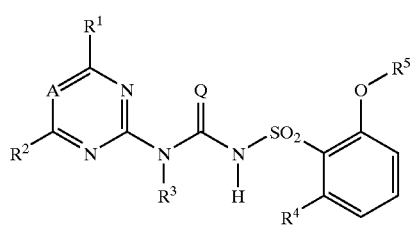

(I)

| Ex. No. | A | Q | $R^1$ | $R^2$ | $R^3$ | $R^4$ | $R^5$ | Melting point (° C.) |
|---|---|---|---|---|---|---|---|---|
| 4 | N | O | $CH_3$ | $OCH_3$ | H | $CF_3$ | $C_2H_5$ | 115 |
| 5 | N | O | $CH_3$ | $OCH_3$ | H | $CF_3$ | $CH_3$ | 214 |
| 6 | N | O | $OCH_3$ | $OCH_3$ | H | $CF_3$ | $CH_3$ | 189 |
| 7 | N | O | $OCH_3$ | $OCH_3$ | H | $CF_3$ | $C_2H_5$ | 176 |
| 8 | CH | O | $CH_3$ | $CH_3$ | H | $CF_3$ | $C_2H_5$ | 214 |
| 9 | N | O | $CH_3$ | $OCH_3$ | H | $CF_3$ | $C_3H_7$-n | 142 |
| 10 | N | O | $OCH_3$ | $OCH_3$ | H | $CF_3$ | $C_3H_7$-n | 162 |
| 11 | CH | O | $CH_3$ | $CH_3$ | H | $CF_3$ | $C_3H_7$-n | 212 |
| 12 | N | O | $CH_3$ | $OCH_3$ | H | $CF_3$ | $C_3H_7$-i | 168 |
| 13 | N | O | $OCH_3$ | $OCH_3$ | H | $CF_3$ | $C_3H_7$-i | 200 |
| 14 | CH | O | $CH_3$ | $CH_3$ | H | $CF_3$ | $C_3H_7$-i | 221 |
| 15 | CH | O | Cl | $OCH_3$ | H | $CF_3$ | $CH_3$ | 224 |
| 16 | CH | O | Cl | $OCH_3$ | H | $CF_3$ | $C_2H_5$ | 176 |

TABLE 1-continued

Examples of compounds of the formula (I)

| Ex. No. | A | Q | $R^1$ | $R^2$ | $R^3$ | $R^4$ | $R^5$ | Melting point (° C.) |
|---|---|---|---|---|---|---|---|---|
| 17 | CH | O | Cl | $OCH_3$ | H | $CF_3$ | $C_3H_7$-n | 169 |
| 18 | N | O | $N(CH_3)_2$ | $OCH_2CF_3$ | H | $CF_3$ | $CH_3$ | 222 |
| 19 | N | O | $N(CH_3)_2$ | $OCH_2CF_3$ | H | $CF_3$ | $C_2H_5$ | 209 |
| 20 | N | O | $N(CH_3)_2$ | $OCH_2CF_3$ | H | $CF_3$ | $C_3H_7$-n | 175 |
| 21 | N | O | $N(CH_3)_2$ | $OCH_2CF_3$ | H | $CF_3$ | $C_3H_7$-i | 204 |
| 22 | CH | O | $OCH_3$ | $OCH_3$ | H | $CF_3$ | $CH_3$ | 111 (decomp.) |
| 23 | CH | O | $OCH_3$ | $OCH_3$ | H | $CF_3$ | $C_2H_5$ | 99 (decomp.) |
| 24 | CH | O | $OCH_3$ | $OCH_3$ | H | $CF_3$ | $C_3H_7$-n | 180 |
| 25 | CH | O | $OCH_3$ | $OCH_3$ | H | $CF_3$ | $C_3H_7$-i | 98 (decomp.) |
| 26 | CH | O | $CH_3$ | $CH_3$ | H | $CH_3$ | $C_2H_5$ | 217 |
| 27 | CH | O | $CH_3$ | $OCH_3$ | H | $CH_3$ | $C_2H_5$ | 183 |
| 28 | CH | O | H | $CH_3$ | H | $CH_3$ | $C_2H_5$ | 190 |
| 29 | CH | O | $CH_3$ | $CH_3$ | H | $CH_3$ | $C_3H_7$-n | 194 |
| 30 | CH | O | H | $CH_3$ | H | $CH_3$ | $C_3H_7$-n | 176 |
| 31 | N | O | $OCH_3$ | $OCH_3$ | H | $CH_3$ | $C_2H_5$ | 181 |
| 32 | N | O | $CH_3$ | $OCH_3$ | H | $CH_3$ | $C_2H_5$ | 170 |
| 33 | CH | O | $CH_3$ | $OCH_3$ | H | $CH_3$ | $C_3H_7$-i | 196 |
| 34[1)] | CH | O | $OCH_3$ | $OCH_3$ | H | $CH_3$ | 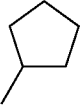 | 204 |
| 35 | CH | O | $CH_3$ | $CH_3$ | H | $CH_3$ | $C_3H_7$-i | 231 |
| 36 | CH | O | $OCH_3$ | $OCH_3$ | H | $CH_3$ | $C_3H_7$-i | 190 |
| 37 | CH | O | H | $CH_3$ | H | $CH_3$ | $C_3H_7$-i | 206 |
| 38 | N | O | $OCH_3$ | $OCH_3$ | H | $CH_3$ | $C_3H_7$-i | 191 |
| 39 | N | O | $OCH_3$ | $OCH_3$ | H | $CH_3$ | $C_3H_7$-i | 205 |
| 40 | N | O | $CH_3$ | $OCH_3$ | H | $CH_3$ | $CH_3$ | 193 |
| 41 | CH | O | $CH_3$ | $CH_3$ | H | $CH_3$ | $CH_3$ | 220 |
| 42 | CH | O | H | $CH_3$ | H | $CH_3$ | $CH_3$ | 206 |
| 43 | CH | O | $CH_3$ | $OCH_3$ | H | $CH_3$ | $CH_3$ | 172 |
| 44 | CH | O | $OCH_3$ | $OCH_3$ | H | $CH_3$ | $CH_3$ | 142 |
| 45 | N | O | $N(CH_3)_2$ | $OCH_2CF_3$ | H | $CH_3$ | $C_2H_5$ | 187 |
| 46 | CH | O | $CH_3$ | $OCH_3$ | H | $CH_3$ | $C_3H_7$-n | 147 |
| 47 | CH | O | $OCH_3$ | $OCH_3$ | H | $CH_3$ | $C_3H_7$-n | 164 |
| 48 | N | O | $OCH_3$ | $OCH_3$ | H | $CH_3$ | $C_3H_7$-n | 156 |
| 49 | N | O | $CH_3$ | $OCH_3$ | H | $CH_3$ | $C_3H_7$-n | 150 |
| 50 | CH | O | $OCH_3$ | $OCH_3$ | H | $C_3H_7$-i | $C_2H_5$ | 184 |
| 51 | N | O | $OCH_3$ | $OCH_3$ | H | $C_3H_7$-i | $C_2H_5$ | 157 |
| 52 | N | O | $N(CH_3)_2$ | $OCH_2CF_3$ | H | $CH_3$ | $CH_3$ | 214 |
| 53 | N | O | $N(CH_3)_2$ | $OCH_2CF_3$ | H | $CH_3$ | $C_3H_7$-i | 202 |
| 54 | CH | O | $OCH_3$ | $OCH_3$ | H | $CH_3$ | 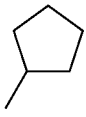 | 171 |
| 55 | N | O | $OCH_3$ | $OCH_3$ | H | $CH_3$ | 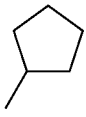 | 198 |

TABLE 1-continued

Examples of compounds of the formula (I)

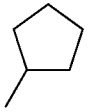

(I)

| Ex. No. | A | Q | $R^1$ | $R^2$ | $R^3$ | $R^4$ | $R^5$ | Melting point (° C.) |
|---|---|---|---|---|---|---|---|---|
| 56 | N | O | $CH_3$ | $OCH_3$ | H | $CH_3$ | 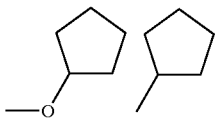 | 183 |
| 57 | N | O | $OCH_3$ | $OCH_3$ | H | $CH_3$ | $C_4H_9$-s | 174 |
| 58 | CH | O | $CH_3$ | $OCH_3$ | H | $CH_3$ | $C_4H_9$-s | 186 |
| 59 | N | O | $CH_3$ | $OCH_3$ | H | $CH_3$ | $C_4H_9$-s | 177 |
| 60 | CH | O | $CH_3$ | $CH_3$ | H | $CH_3$ | $C_4H_9$-s | 228 |
| 61 | CH | O | $OCH_3$ | $OCH_3$ | H | $CH_3$ | $C_4H_9$-s | 207 |
| 62 | CH | O | $CH_3$ | $CF_3$ | H | $CH_3$ | $C_3H_7$-i | 192 |
| 63 | CH | O | $CH_3$ | $CF_3$ | H | $CH_3$ | $CH_3$ | 209 |
| 64 | N | O | $CH_3$ | $OCH_3$ | H | $C_3H_7$-i | $CH_3$ | 136 |
| 65 | CH | O | $OCH_3$ | $OCH_3$ | H | $CH_3$ | $CHF_2$ | 170 |
| 66 | N | O | $CH_3$ | $OCH_3$ | H | $CH_3$ | $CHF_2$ | 197 |
| 67 | N | O | $OCH_3$ | $OCH_3$ | H | $OC_3H_7$-n | $C_3H_7$-n | 140 |
| 68 | CH | O | Cl | $OCH_3$ | H | $OCH_3$ | $C_3H_7$-i | 148 |
| 69 | N | O | $CH_3$ | $OCH_3$ | H | $OCH_3$ | $C_3H_7$-i | 152 |
| 70 | N | O | $CH_3$ | $OCH_3$ | H | $OC_4H_9$-n | $C_4H_9$-n | 90 |
| 71 | N | O | $CH_3$ | $OCH_3$ | H | $OC_3H_7$-i | $C_3H_7$-i | 80 |
| 72 | N | O | $CH_3$ | $OCH_3$ | H | $OC_2H_5$ | $C_3H_7$-i | 118 |
| 73 | N | O | $CH_3$ | $OCH_3$ | Na | $OCH_3$ | $CH_3$ | 203 |
| 74 | CH | O | $OCH_3$ | $OCH_3$ | H | $C_3H_7$-i | $CH_3$ | 164 |
| 75 | CH | O | $OCH_3$ | $OCH_3$ | H | $C_3H_7$-i | $C_3H_7$-n | 157 |
| 76 | CH | O | $CH_3$ | $CF_3$ | H | $CH_3$ | $C_2H_5$ | 179 |
| 77 | N | O | $CH_3$ | $CH_3$ | H | $CF_3$ | $CH_3$ | 155 |
| 78 | N | O | $CH_3$ | $SCH_3$ | H | $CF_3$ | $CH_3$ | 178 |
| 79 | N | O | $CH_3$ | $N(CH_3)_2$ | H | $CF_3$ | $CH_3$ | 213 |
| 80 | N | O | $CH_3$ | $OC_2H_5$ | H | $CF_3$ | $CH_3$ | 121 |
| 81 | N | O | $C_2H_5$ | $OCH_3$ | H | $CF_3$ | $CH_3$ | 117 |
| 82 | N | O | $OCH_2CF_2CHF_2$ | $N(CH_3)_2$ | H | $CF_3$ | $CH_3$ | 185 |
| 83 | N | O | $CH_3$ | $OCH_3$ | Na | $C_3H_7$-i | $CH_3$ | 170 |
| 84 | N | O | $OCH_3$ | $OCH_3$ | H | $C_3H_7$-i | $C_3H_7$-n | 149 |
| 85 | N | O | $OCH_3$ | $OCH_3$ | H | $C_3H_7$-i | $CH_3$ | 187 |
| 86 | N | O | $CH_3$ | $OCH_3$ | H | $C_3H_7$-i | $C_2H_5$ | 163 |
| 87 | CH | O | $CH_3$ | $OCH_3$ | H | $C_3H_7$-i | $CH_3$ | 175 |
| 88 | CH | O | $CH_3$ | $OCH_3$ | H | $C_3H_7$-i | $C_3H_7$-i | 152 |
| 89 | CH | O | $OCH_3$ | $OCH_3$ | H | $C_3H_7$-i | $C_3H_7$-i | 138 |
| 90 | N | O | $CH_3$ | $OCH_3$ | Na | $CH_3$ | $CH_3$ | 149 |
| 91 | N | O | $CH_3$ | $CH_3$ | H | 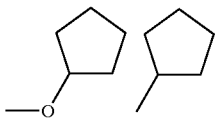 | | 125 |
| 92 | N | O | $CH_3$ | $OCH_3$ | Na | $OC_3H_7$-i | $C_3H_7$-i | 178 |
| 93 | N | O | Cl | $OCH_3$ | Na | $OCH_3$ | $C_3H_7$-i | 172 |
| 94 | N | O | $CH_3$ | $OCH_3$ | Na | $OC_2H_5$ | $C_2H_5$ | 145 |
| 95[2)] | N | O | $CH_3$ | $OCH_3$ | Na | $OCH_3$ | $C_3H_7$-n | NMR data |
| 96 | N | O | $OCH_3$ | $OCH_3$ | H | $OCH_3$ | $C_2H_5$ | 110 |
| 97 | N | O | $OCH_3$ | $OCH_3$ | H | $OC_2H_5$ | $C_2H_5$ | 142 |
| 98 | N | O | $OCH_3$ | $OCH_3$ | H | $OCH_3$ | $C_3H_7$-n | 188 |
| 99 | N | O | $OCH_3$ | $OCH_3$ | H | $OC_2H_5$ | $C_4H_9$-s | 136 |
| 100 | CH | O | Cl | $OCH_3$ | H | $OCH_3$ | $C_2H_5$ | 146 |
| 101 | CH | O | Cl | $OCH_3$ | H | $OCH_3$ | $C_3H_7$-n | 110 |
| 102 | CH | O | Cl | $OCH_3$ | H | $OCH_3$ | $C_4H_9$-n | 117 |
| 103 | CH | O | Cl | $OCH_3$ | H | $OC_4H_9$-n | $C_4H_9$-n | 135 |
| 104 | CH | O | Cl | $OCH_3$ | H | $OC_2H_5$ | $C_4H_9$-n | 128 |

TABLE 1-continued

Examples of compounds of the formula (I)

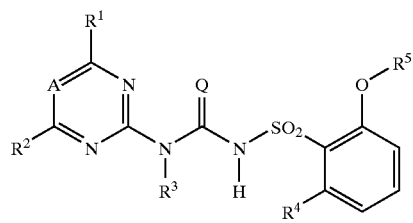

(I)

| Ex. No. | A | Q | R¹ | R² | R³ | R⁴ | R⁵ | Melting point (° C.) |
|---|---|---|---|---|---|---|---|---|
| 105 | N | O | CH₃ | OCH₃ | H | OC₂H₅ | C₃H₇-n | 110 |
| 106 | N | O | CH₃ | OCH₃ | H | OCH₃ | CH₃ | 177 |
| 107 | N | O | CH₃ | OCH₃ | H | OCH₃ | 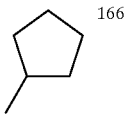 | 166 |
| 108 | N | O | CH₃ | OCH₃ | H | OC₂H₅ | C₄H₉-i | 85 |
| 109 | N | O | CH₃ | OCH₃ | H | OCH₃ | C₂H₅ | 148 |
| 110 | N | O | CH₃ | OCH₃ | H | OCH₃ | C₄H₉-n | 125 |
| 111 | N | O | CH₃ | OCH₃ | H | OC₂H₅ | 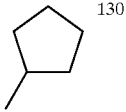 | 130 |
| 112 | CH | O | OCH₃ | OCH₃ | H | CH₃ | CF₃ | 178 |
| 113 | N | O | CH₃ | OCH₃ | H | CH₃ | CF₃ | 178 |
| 114 | CH | O | OCH₃ | OCH₃ | H | C₂H₅ | CF₃ | 147 |
| 115 | N | O | CH₃ | OCH₃ | H | C₂H₅ | CF₃ | 140 |
| 116 | CH | O | OCH₃ | OCH₃ | H | CH₃ | CF₂CHF₂ | 169 |
| 117 | N | O | CH₃ | OCH₃ | H | CH₃ | CF₂CHF₂ | 184 |
| 118 | CH | O | OCH₃ | OCH₃ | H | CH₃ | CH₂CF₃ | 184 |
| 119 | N | O | CH₃ | OCH₃ | H | CH₃ | CH₂CF₃ | 178 |
| 120 | CH | O | OCH₃ | OCH₃ | H | C₂H₅ | CHF₂ | 110 |
| 121 | N | O | CH₃ | OCH₃ | H | C₂H₅ | CHF₂ | 157 |
| 122 | CH | O | OCH₃ | OCH₃ | H | C₃H₇-n | CF₃ | 147 |
| 123 | N | O | CH₃ | OCH₃ | H | C₃H₇-n | CF₃ | 77 |

Notes:

[1] In Example 34,  is propargyl = CH₂—C≡CH

[2] NMR data for Example 95: ¹H-NMR (300MHz; D₂O): δ = 0.96 (t, CH₃); 1.77 (m, O—CH₂—CH₂—CH₃); 2.42 (s, CH₃); 3.87 (s, OCH₃); 3.98 (s, OCH₃); 4.04 (t, O—CH₂—); 6.79 (brd.d, 2 aromat. H); 7.48 (brd.t, 1 aromat. H) ppm.

Starting Material of the Formula (III):

Example (III-1)

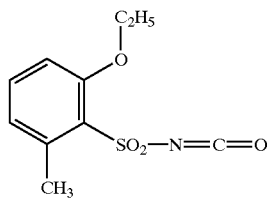

21.5 g (0.1 mol) of 2-ethoxy-6-methyl-benzenesulphonamide and 10 g (0.1 mol) of n-butyl isocyanate are heated to the boil in 100 ml of chlorobenzene. At reflux temperature, phosgene is introduced for 4 hours. The clear solution is concentrated under reduced pressure and the residue is subjected to precision distillation. At a pressure of 0.8 mbar and an overhead temperature of 135–140° C., 2-ethoxy-6-methyl-phenylsulphonyl isocyanate passes over and solidifies in the receiving flask.

This gives 7.9 g of 2-ethoxy-6-methyl-phenylsulphonyl isocyanate as a colourless product of melting point 40° C.

Starting Materials of the Formula (IV):

Example (IV-1)

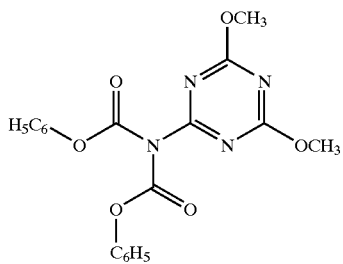

70 g (0.44 mol) of phenyl chloroformate are added dropwise with stirring to a mixture of 31 g (0.20 mol) of 2-amino-4,6-dimethoxy-s-triazine and 100 ml of pyridine. The reaction mixture is stirred at 20° C. to 25° C. for about 15 hours and subsequently concentrated using water pump vacuum. The residue is taken up in water and then acidified using conc. hydrochloric acid. The resulting crystalline product is isolated by filtration with suction.

This gives 74.2 g (91% of theory) of 2-(N,N-bis-phenoxycarbonyl-amino)-4,6-dimethoxy-s-triazine of melting point 125° C.

Starting Materials of the Formula (V):

Example (V-1)

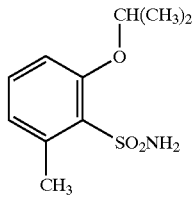

At 20° C., 64.6 g (0.26 mol) of 2-isopropoxy-6-methyl-benzenesulphonyl chloride are stirred in 350 ml of 25% strength aqueous ammonia solution for 12 hours. The resulting crystalline product is subsequently isolated by filtration with suction.

This gives 54 g (90% of theory) of 2-isopropoxy-6-methyl-benzenesulphonamide of melting point 78° C.

Use Examples

Example A

Pre-emergence Test

| Solvent: | 5 parts by weight of acetone |
| --- | --- |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of the active compound. Advantageously, the amount of water per unit area is kept constant. The active compound concentration in the preparation is not important, only the active compound application rate per unit area is critical.

After three weeks, the degree of damage to the plants is rated in % damage in comparison with the development of the untreated control.

The figures denote:

0%=no effect (like untreated control)
100%=total destruction

In this test, for example, the compounds of Preparation Example 1, 2, 3, 4, 5, 6, 7, 8, 9, 10, 11, 12, 13, 14, 15, 16, 22, 27, 31, 32, 33, 34, 38, 39, 40, 41, 43, 44, 46, 48, 49, 56, 65 and 66 exhibit, at application rates between 30 g and 125 g of a.i. per hectare, very strong activity against weeds.

"a.i."="active ingredient"

TABLE A

Pre-emergence test/greenhouse

| Active compound of Preparation Example No. | Application rate (g of ai./ha) | Alope- curus | Lo- lium | Sor- ghum | Amaran- thus | Cheno- podium | Stel- laria |
|---|---|---|---|---|---|---|---|
| 4 | 60 | 100 | 100 | 100 | 100 | 100 | 95 |
| 5 | 60 | 100 | 100 | 100 | 100 | 100 | 100 |
| 6 | 60 | 100 | 100 | 100 | 100 | 100 | 100 |
| 7 | 60 | 100 | 95 | 100 | 95 | 100 | 95 |
| 1 | 60 | 100 | 100 | 100 | 100 | 100 | 100 |
| 8 | 30 | 100 | 100 | 100 | — | 80 | 90 |
| 9 | 30 | 100 | 100 | 90 | 100 | 100 | 100 |
| 10 | 60 | 100 | 100 | 100 | 100 | 100 | 100 |
| 11 | 60 | 100 | 100 | 100 | 100 | 100 | 95 |
| 12 | 30 | 100 | 100 | 100 | 100 | 95 | 100 |
| 13 | 60 | 100 | 100 | 100 | 100 | 100 | 100 |
| 14 | 30 | 100 | 100 | 95 | — | 95 | 95 |
| 15 | 60 | 100 | 95 | 95 | 95 | 100 | 95 |
| 16 | 30 | 100 | — | 80 | — | 100 | 90 |
| 22 | 30 | 100 | — | 95 | 100 | 100 | 100 |
| 27 | 60 | 100 | 100 | 100 | 100 | 100 | 100 |
| 3 | 60 | 95 | 60 | 80 | 80 | 95 | 95 |
| 31 | 60 | 95 | 100 | 90 | 95 | 100 | 95 |
| 32 | 60 | 95 | 100 | 95 | 100 | 100 | 100 |
| 33 | 30 | 100 | 95 | 100 | — | 70 | 90 |
| 34 | 30 | 100 | — | 90 | — | 90 | 90 |
| 38 | 30 | 100 | 100 | 100 | 80 | 100 | 100 |
| 39 | 30 | 100 | 100 | 100 | 100 | 100 | 100 |
| 40 | 30 | 100 | 100 | 100 | 100 | 100 | 100 |
| 41 | 30 | 95 | 100 | 100 | 60 | 100 | 80 |
| 43 | 30 | 100 | 100 | 100 | 100 | 100 | 100 |
| 44 | 30 | 100 | 100 | 100 | 100 | 100 | 100 |
| 2 | 30 | 100 | 100 | 100 | 100 | 100 | 100 |
| 46 | 60 | 100 | 90 | 100 | 90 | 100 | 80 |
| 48 | 60 | 100 | 100 | 100 | 100 | 100 | 100 |
| 49 | 30 | 100 | 100 | 100 | 100 | 100 | 100 |
| 56 | 60 | 100 | 100 | 90 | 100 | 100 | 100 |
| 65 | 125 | 95 | 70 | — | 95 | 95 | 95 |
| 66 | 60 | 95 | 95 | 95 | 95 | 95 | 95 |

Example B

Post-emergence Test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the amounts of active compound desired in each case are applied in 1000 l of water/ha.

After three weeks, the degree of damage to the plants is rated in % damage in comparison with the development of the untreated control.

The figures denote:

0%=no effect (like untreated control)
100%=total destruction

In this test, for example, the compounds of Preparation Example 2, 3, 4, 5, 6, 7, 8, 9, 12, 15, 16, 17, 22, 23, 24, 25, 27, 31, 32, 34, 38, 39, 40, 41, 43, 44, 48, 49, 51, 65 and 66 exhibit very strong activity against weeds.

TABLE B

Post-emergence test/greenhouse

| Active compound of Preparation Example No. | Application rate (g of ai./ha) | Alope- curus | Echino- chloa | Abu- tilon | Matri- caria |
|---|---|---|---|---|---|
| 4 | 30 | 90 | 90 | 100 | 100 |
| 5 | 30 | 80 | 100 | 100 | 100 |
| 6 | 30 | 60 | 100 | 90 | 100 |
| 7 | 30 | 95 | 95 | 95 | 100 |
| 8 | 30 | 80 | 90 | 90 | 100 |
| 9 | 8 | 90 | 80 | 100 | 95 |
| 12 | 30 | 95 | 90 | 95 | 100 |
| 15 | 60 | 70 | 90 | 95 | 100 |
| 16 | 30 | 70 | 70 | 100 | 100 |
| 17 | 30 | — | 70 | 90 | 95 |
| 22 | 30 | 60 | 80 | 95 | 95 |
| 23 | 30 | 60 | 70 | 95 | 95 |
| 24 | 30 | 60 | 70 | 95 | 95 |
| 25 | 30 | 60 | 70 | 95 | 90 |
| 27 | 60 | 95 | 95 | 100 | 90 |
| 3 | 60 | 90 | 80 | 100 | 95 |
| 31 | 60 | 80 | 80 | 100 | 100 |
| 32 | 60 | 70 | 90 | 100 | 100 |
| 34 | 30 | 60 | 80 | 90 | 90 |
| 38 | 30 | 60 | 70 | 95 | 95 |
| 39 | 30 | 90 | 95 | 100 | 100 |
| 40 | 30 | 100 | 95 | 95 | 100 |
| 41 | 30 | 60 | 95 | 90 | 70 |
| 43 | 30 | 60 | 95 | 100 | 100 |
| 44 | 30 | 60 | 90 | 100 | 100 |
| 2 | 30 | 90 | 90 | 95 | 100 |
| 48 | 60 | 95 | 70 | 100 | 90 |
| 49 | 30 | 90 | 80 | 100 | 100 |
| 51 | 60 | 80 | 90 | 100 | 90 |
| 65 | 125 | 90 | 90 | 100 | 100 |
| 66 | 60 | 80 | 80 | 100 | 100 |

What is claimed is:
1. A compound of formula (I)

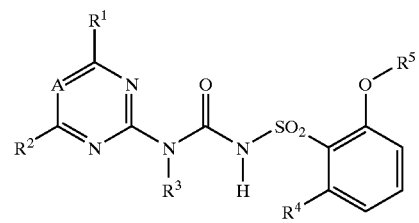

in which
A represents a CH grouping,
Q represents oxygen or sulphur,
$R^1$ represents hydrogen, halogen, represents respectively optionally cyano-, halogen- or $C_1$–$C_4$-alkoxy-substituted alkyl, alkoxy, alkylthio, alkylamino or dialkylamino having in each case 1 to 4 carbon atoms in the alkyl groups, represents respectively optionally cyano-, halogen-, $C_1$–$C_4$-alkyl- or $C_1$–$C_4$-alkoxy-substituted cycloalkyl or cycloalkyloxy having in each case 3 to 6 carbon atoms, or represents respectively optionally cyano-, halogen-, $C_1$–$C_4$- alkyl- or $C_1$–$C_4$-alkoxy-substituted oxetanyloxy, furyloxy or tetrahydrofuryloxy, $R^2$ represents respectively optionally cyano-, halogen- or $C_1$–$C_4$-alkoxy-substituted alkyl, alkoxy, alkylthio, alkylamino or dialkylamino having in each case 1 to 4 carbon atoms in the alkyl groups, represents respectively optionally cyano-, halogen-, $C_1$–$C_4$-alkyl- or $C_1$–$C_4$-alkoxy-substituted cycloalkyl or cycloalkyloxy having in each case 3 to 6 carbon atoms, or represents respectively optionally cyano-, halogen-, $C_1$–$C_4$-alkyl- or $C_1$–$C_4$-alkoxy-substituted oxetanyloxy, furyloxy or tetrahydrofuryloxy, $R^3$ represents hydrogen or optionally $C_1$–$C_4$-alkoxy, $C_1$–$C_4$-alkyl-carbonyl- or $C_1$–$C_4$-alkoxy-carbonyl-substituted alkyl having 1 to 4 carbon atoms, $R^4$ represents halogen-substituted $C_1$–$C_6$alkyl, $R^5$ represents hydrogen, formyl, represents respectively optionally cyano-, halogen- or $C_1$–$C_4$-alkoxy-substituted alkyl, alkylcarbonyl, alkoxycarbonyl or alkylsulphonyl having in each case 1 to 6 carbon atoms in the alkyl groups, represents respectively optionally halogen-substituted alkenyl or alkinyl having in each case 2 to 6 carbon atoms, represents respectively optionally cyano-, halogen- or $C_1$–$C_4$-alkyl-substituted cycloalkyl, cycloalkylcarbonyl or cycloalkylsulphonyl having in each case 3 to 6 carbon atoms in the cycloalkyl groups, or represents respectively optionally cyano-, halogen-, $C_1$–$C_4$-alkyl- or $C_1$–$C_4$-alkoxy-substituted oxetanyl, furyl or tetrahydrofuryl, or a salt of the compound of formula (I).

2. A compound of formula (I) according to claim 1, wherein

A represents a CH grouping,

Q represents oxygen or sulphur, $R^1$ represents hydrogen, fluorine, chlorine, bromine or respectively optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylamino, ethylamino, n- or i-propylamino, dimethylamino or diethylamino, $R^2$ represents fluorine, chlorine, bromine or respectively optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylamino, ethylamino, n- or i-propylamino, dimethylamino or diethylamino, $R^3$ represents hydrogen or optionally methoxy-, ethoxy-, n- or i-propoxy-, acetyl-, propionyl-, n- or i-butyroyl-, methoxycarbonyl-, ethoxycarbonyl-, n- or i-propoxycarbonyl-substituted methyl or ethyl, $R^4$ represents fluorine-, or chlorine-, substituted methyl, ethyl, n- or i-propyl, n-, i-, s- or t-butyl, $R^5$ represents hydrogen, formyl, represents respectively optionally cyano-, fluorine-, chlorine-, methoxy-, ethoxy-, n- or i-propoxy-substituted methyl, ethyl, n- or i-propyl, n-, i-, s- or t-butyl, acetyl, propionyl, n- or i-butyroyl, methoxycarbonyl, ethoxycarbonyl, n- or i-propoxycarbonyl, methylsulphonyl, ethylsulphonyl, n- or i-propylsulphonyl, represents respectively optionally fluorine-, chlorine- or bromine-substituted propenyl, butenyl, propinyl or butinyl, or represents respectively optionally cyano-, fluorine-, chlorine-, bromine-, methyl-, ethyl-, n- or i-propyl-substituted cyclopropyl, cyclobutyl, cyclopentyl, cyclohexyl, cyclopropylcarbonyl, cyclobutylcarbonyl, cyclopentylcarbonyl, cyclohexylcarbonyl, cyclopropylsulphonyl, cyclobutylsulphonyl, cyclopentylsulphonyl or cyclohexylsulphonyl, or the sodium, potassium, magnesium, calcium, ammonium, $C_1$–$C_4$alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salt of the compound of formula (I).

3. A compound of the formula (I)

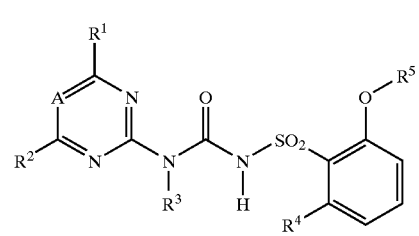

(I)

wherein:

A is a CH grouping,

Q is oxygen, $R^1$ is selected from the group consisting of hydrogen, halogen, $C_1$–$C_4$-alkyl, $C_1$–$C_4$-dialkylamino and optionally halogen-substituted $C_1$–$C_4$-alkoxy, $R^2$ is selected from the group consisting of $C_1$–$C_4$-alkyl, $C_1$–$C_4$-alkythio, $C_1$–$C_4$-dialkylamino and optionally halogen-substituted $C_1$–$C_4$-alkoxy, $R^3$ is hydrogen, $R^4$ is halogen-substituted $C_1$–$C_6$alkyl, $R^5$ is optionally halogen-substituted $C_1$–$C_4$-alkyl or represents a $C_3$–$C_6$-cycloalkyl, or the sodium, potassium, magnesium, calcium, ammonium $C_1$–$C_4$-alkyl-ammonium, di-($C_1$–$C_4$alkyl)-ammonium, tri-($C_1$–$C_4$-alkyl)-ammonium, tetra-($C_1$–$C_4$)-ammonium, tri-($C_1$–$C_4$-alkyl)-sulphonium, $C_5$ or $C_6$-cycloalkyl-ammonium and di-($C_1$–$C_2$alkyl)-benzyl-ammonium salt of the compound of formula (I).

4. The compound of formula (I) according to claim 3, wherein:

A is a CH grouping,

Q is oxygen, $R^1$ selected from the group consisting of hydrogen, fluorine, chlorine, bromine, methyl, ethyl, n-propyl, i-propyl, dimethylamino, diethylamino, methoxy, ethoxy, n-propoxy and i-propoxy, wherein methoxy, ethoxy, n-propoxy and i-propoxy are optionally substituted with fluorine or chlorine, $R^2$ is selected from the group consisting of methyl, ethyl, n-propyl, i-propyl, methylthio, ethylthio, n-propylthio, i-propylthio, dimethylamino, diethylamino, methoxy, ethoxy, n- and i-propoxy, wherein methoxy, ethoxy, n-propoxy and i-propoxy are optionally substituted with fluorine or chlorine, $R^3$ is hydrogen, $R^4$ is selected from the group consisting of: fluorine- or chlorine-substituted methyl, ethyl, n-propyl, i-propyl, n-butyl, i-butyl, s-butyl, t-butyl, $R^5$ is (a) optionally fluorine- or chlorine-substituted methyl, ethyl, n-propyl, i-propyl, n-butyl, i-butyl, s-butyl, t-butyl; or (b) cyclopropyl, cyclobutyl, cyclopentyl or cyclohexyl.

5. A compound of formula (I)

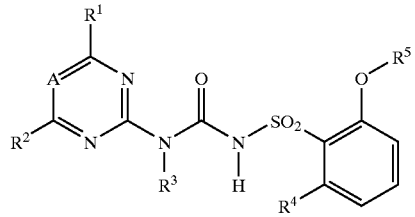

wherein:

A is a CH grouping,

Q is oxygen, $R^1$ is selected from the group consisting of hydrogen, methyl, chlorine, methoxy and oxetanyl, $R^2$ is selected from the group consisting of methyl, methoxy, chlorine and oxetanyl, $R^3$ is hydrogen, $R^4$ is trifluoromethyl, $R^5$ is selected from the group consisting of methyl, diffluoromethyl, trifluoromethyl, ethyl, methoxy, n-propyl, i-propyl, cyclopentanyloxy and oxetanyl, or the sodium, potassium, magnesium, calcium, ammonium, $C_1$–$C_4$-alkyl-ammonium, di-($C_1$–$C_4$) alkyl)-ammonium, tri($C_1$–$C_4$)-ammonium, tetra-($C_1$–$C_4$)-ammonium, tetra-($C_1$–$C_4$alkyl)-sulphonium, $C_5$- or $C_6$-cycloalkyl-ammonium and di-($C_1$–$C_2$alkyl)-benzyl-ammonium salt of the compound of formula (I).

6. A compound of formula (I), wherein:

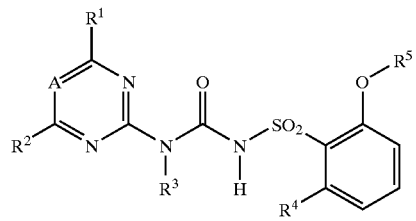

A is a CH grouping,

Q is oxygen, $R^1$ is selected from the group consisting of hydrogen, methyl, methoxy and chlorine, $R^2$ is selected from the group consisting of methyl and methoxy, $R^3$ is hydrogen, $R^4$ is selected from the group consisting of trifluoromethyl, $R^5$ is selected from the group consisting of methyl, difluoromethyl, trifluoromethyl, ethyl, —$CF_2CHF_2$, —$CH_2CF_3$, n-propyl, i-propyl, s-butyl, propargyl and cyclopentanyl.

7. Herbicidal compositions, which is comprised of one or more compound of the formula (I) according to claim 1 and a herbicidally acceptable carrier or diluent.

8. The method for controlling undesirable plant growth which comprises of administering an effective amount of one or more compound of formula (I) according to claim 1.

9. A method for controlling weeds wherein an effective amount of compound formula (I) according to claim 1 are allowed to act on the weeds or their habitat.

* * * * *